United States Patent [19]

Chidester

[11] Patent Number: 4,517,473
[45] Date of Patent: May 14, 1985

[54] SOLID-STATE AUTOMATIC INJECTION CONTROL DEVICE

[75] Inventor: Dale H. Chidester, Levittown, Pa.

[73] Assignee: American Cyanamid Company, Stamford, Conn.

[21] Appl. No.: 383,633

[22] Filed: Jun. 1, 1982

[51] Int. Cl.³ .................... H03K 13/00; H03K 17/18; H03K 17/296
[52] U.S. Cl. .................... 307/269; 307/518; 307/597; 328/119; 377/2
[58] Field of Search .................... 307/269, 518, 597; 328/119; 377/2

[56] References Cited

U.S. PATENT DOCUMENTS

| | | | |
|---|---|---|---|
| 3,710,262 | 1/1973 | Sorensen | 307/269 |
| 3,883,687 | 5/1975 | Stenstrom | 307/269 |
| 3,959,730 | 5/1976 | Weber et al. | 307/269 |

*Primary Examiner*—John S. Heyman
*Attorney, Agent, or Firm*—Estelle J. Tsevdos; Alphonse R. Noë

[57] ABSTRACT

In order to control the auto-sampler in a device such as a gas chromatograph in which data is sampled by an analog-to-digital converter, the converter providing outputs indicative of its status and having one state when the converter is enabled, another state when the converter is disabled and pulsing between said states when the converter is acquiring data, an automatic injection control device is provided which: counts the sampling pulses from the converter to insure that a full conversion cycle has been completed and sets a first signal to so indicate; through a retriggerable, one-shot multivibrator insures that the last of the sampling pulses is completed and provides a second signal accordingly; and adds these two signals with the status signal indicating that the converter is in a condition to receive data to provide a trigger signal for use by the auto-sampler.

Further, a method for generating triggering signals to initiate such event is presented.

17 Claims, 3 Drawing Figures

SOLID-STATE AUTOMATIC INJECTION CONTROL DEVICE

BACKGROUND OF THE INVENTION

This invention relates to automatic injection controls in general and more particularly to a solid state timing device particularly adapted for use as an automatic injection control.

In the field of analytical instruments, an automatic injection control device is used, for example, in conjunction with a chromatograph, liquid and/or gas, particularly gas chromatograph, which is coupled to an analog-to-digital converter module and an auto-sampler. The analog-to-digital converter module includes a status output which generates a steady signal when the converter is ready to acquire data, generates pulses while the converter is acquiring data and is off when the analog-to-digital converter is not in a condition to acquire data. In addition, during other times in the course of operation, the converter status output will cease to function momentarily.

In operation, it is desired to operate the autosampler at a time when the converter is capable of receiving data and to prevent operation of the auto-sampler during the data acquisition phase. This reqires an automatic injection control device which will be responsive to the status signal and provide an appropriate trigger output to the auto-sampler.

Thus, it is the object of the present invention to provide such an automatic injection control device which is particularly useful in conjunction with a chromatograph such as a gas chromatograph.

It is an object to provide such a device which provides at its output different types of signals so that it may be used in different applications.

It is also an object of the present invention to provide a solid state timing device which is responsive to a status signal and which, from that status signal, can generate an appropriate trigger signal in order to effectively synchronize control and regulate a predetermined cyclic operation of an instrument or the like.

Further, it is an object of this invention to provide a method for generating triggering signals to synchronize data in an instrument such as a gas chromatograph.

SUMMARY OF THE INVENTION

In accordance with the present invention, these objects are accomplished in an automic device for use in an instrument which includes a means responsive to a trigger signal to initiate an event; and a data acquisition means adapted to receive and convert data resulting from that event. The data acquisition means has a status output which is in one state when it is available to receive data and in another state when it is not available to receive data and which is pulsed during a conversion cycle. The automatic timing device synchronizes operation of a means responsive to trigger the data acquisition means by providing a means to count the pulses occuring during a conversion cycle and thereby provides a first output signal during a predetermined count; provides a second output signal at a predetermined time after the last pulse is received; and then ANDING the status signal in the one state, the first output signal and the second output signal to provide a trigger output when all three signals are present. This trigger signal is provided only when the data acquisition means can receive an input, and data are not being acquired.

As is seen, this device receives a status signal; effectively decodes this signal to determine the state of an analog-to-digital converter providing the signal; and supplies triggering outputs in accordance with this decoding. More specifically, the status input is fed to a retriggerable, one-shot multivibrator which has a time period longer than the time between pulses when the converter is pulsing to indicate data acquisition. Thus, the retriggerable one-shot will provide an output for as long as data acquisition occurs. In addition, the circuit includes a counter, to count the number of pulses output to insure that a complete conversion takes place. When the required count is reached, an "arm" flip-flop is set. The final output of the circuit, i.e., the trigger signal is generated in an ANDING operating which is enabled by an output from the "arm" flip-flop. Other required inputs are those indicating no further triggering of the one-shot and an appropriate level of the status signal from the converter. Thus, the circuit prevents the autosampler from prematurely injecting the next sample, but at the same time insures repeated injections of sample at the appropriate time, to increase sample throughput and eliminate the loss of synchronization between data acquisition and sample injection.

The device of the present invention provides different types of outputs and thus may be used with a variety of auto-samplers whose cyclic operation depends on external trigger signals. It may also be used for the control of other instruments and devices which must be triggered or turned on or off under certain predetermined conditions and time intervals.

DETAILED DESCRIPTION

Figure 1:
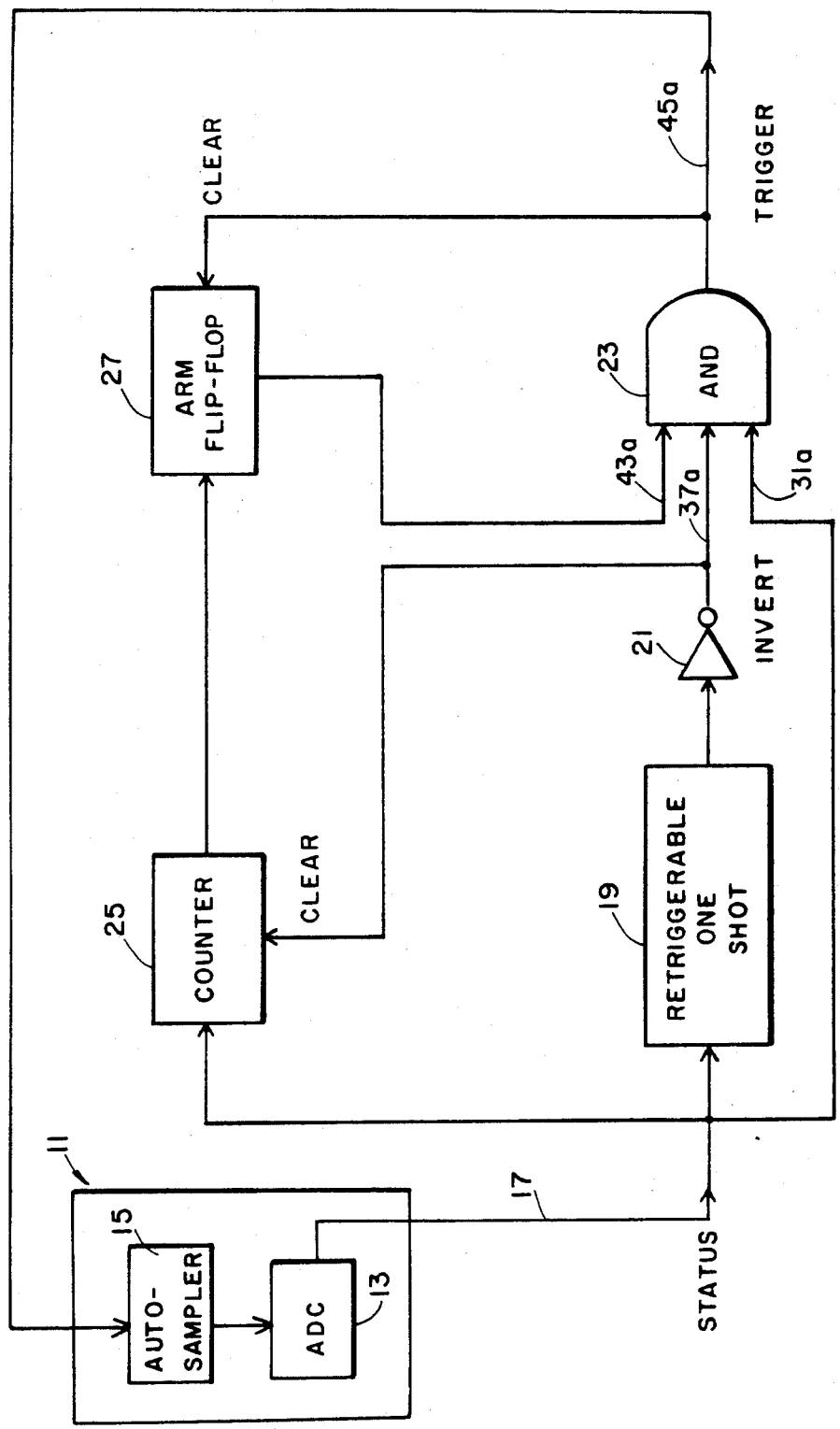
FIG. 1 is an overall block diagram of the solid state automatic injection apparatus of the present invention.

As one embodiment of the present invention, the block diagram of FIG. 1 illustrates a gas chromatograph 11 which includes an analog-to-digital converter 13 and an auto-sampler 15. Converter 13 provides a status output on line 17. The status output is at one logic level when the converter is ready to receive information, pulses during the receipt of information and is at the other logic level if the converter is not in a position to receive data. The status output is provided as an input to a retriggerable, one-shot multivibrator 19. The multivibrator 19 has a time period greater than the time between status pulses when data acquisition is taking place. The output of the retriggerable, one-shot is inverted through an inverter 21 and provided as one input to an AND gate 23. The status output is provided as another input to AND gate 23 and as a count input to a counter 25. Counter 25 is cleared by the output of inverter 21. The output of counter 25, which will occur after a certain number of pulses are counted, is provided as an input to an "arm" flip-flop 27, which provides the third input to AND gate 23. The output of AND gate 23 is the trigger signal which is coupled back to the auto-sampler 156. In addition, it provides a clear signal for the "arm" flip-flop 27.

Figure 2:
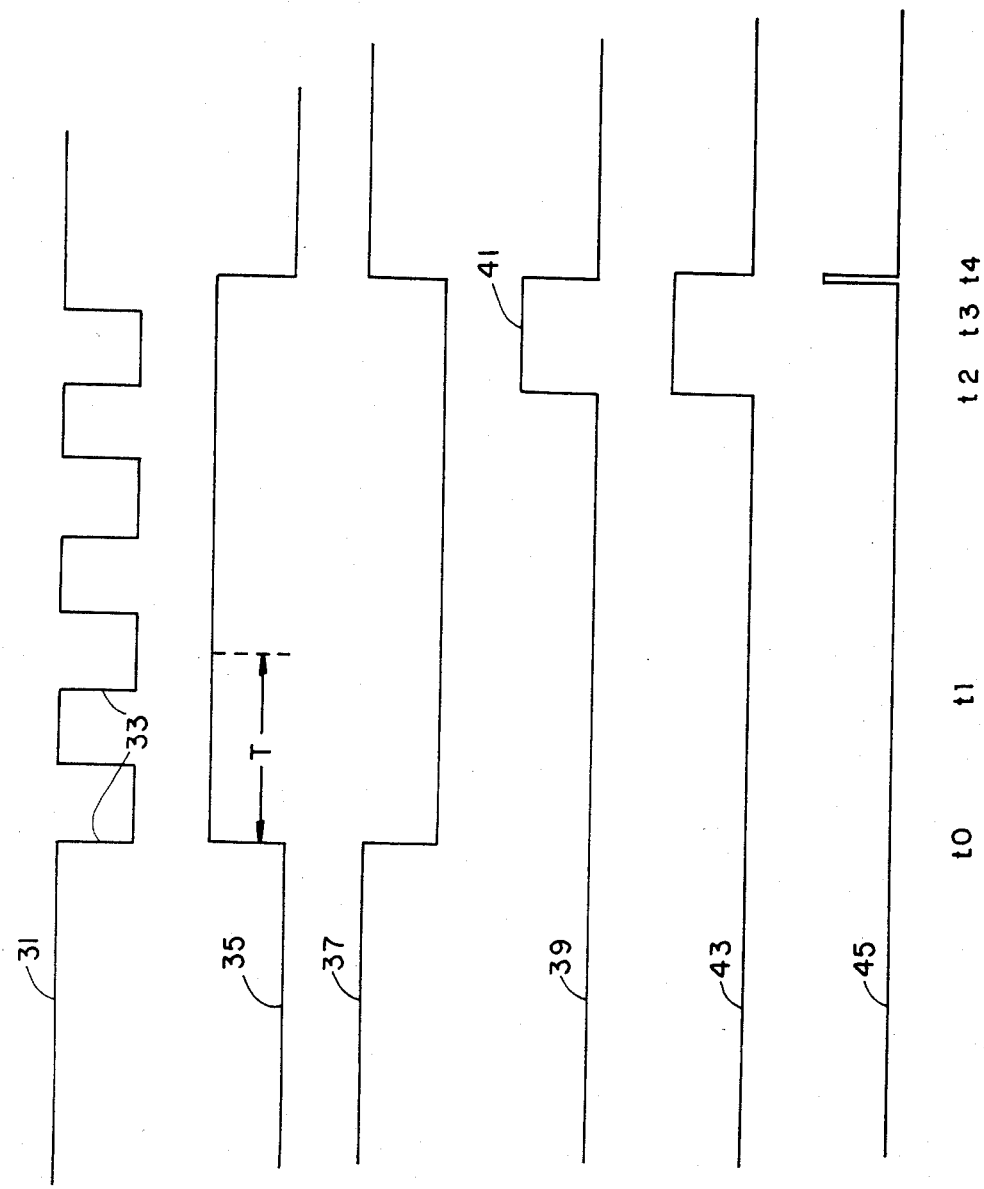
FIG. 2 is a timing diagram illustrating the timing signals occurring in conjunction with FIG. 1.

The operation of this circuit is best demonstrated by the timing diagram of FIG. 2. Assume that a data acquisition cycle has just begun. For sake of example, it will be assumed that there are only four pulse cycles although, as will become clear from the detailed description of FIG. 3 below, one embodiment utilizes a divide-by-twelve counter to, in effect, count twelve pulses. The status signal is indicated as waveform 31 of FIG. 2. In this example, it is assumed that a high logic level indicates readiness to receive data. Thus, the four pulses 33, occurring during an acquisition phase, are negative going pulses. Again, it is assumed that the retriggerable, one-shot 19 triggers on a negative going edge. Thus, at time t0 one-shot 19 will be triggered as indicated by waveform 35. One-shot 19 has a time period indicated by the time T which is greater than the time between two negative going edges, i.e., the time between t0 and t1. Thus, before one-shot times out, a further negative going pulse 33 will occur to retrigger it. This continues to occur until the end of the last pulse at time t3. Shortly after that time, at time t4, the output of retriggerable, one-shot 19 will go low again. This signal, i.e., the signal of waveform 35, is inverted by inverter 21. Thus, the output from inverter 21 will appear as shown on waveform 37. In the beginning, counter 35 had a low output as indicated by waveform 39. The output remains low until the fourth count, at which time, i.e., at time t2, it goes high. It remains high until the output of inverter 21 goes high to clear it, i.e., until time t4. Thus, a pulse 41 is generated which sets flip-flop 27 as indicated by waveform 43. AND gate 23 has as inputs the signals corresponding to waveforms 31, 37 and 43 and will provide an output whenever these signals are high. These have been labeled as 31a, 37a and 43a on FIG. 1. Thus, at time t4, when the output on line 37a goes high, all three signals are high and the trigger signal shown by waveform 45, indicated by line 45a in FIG. 1, is generated. The trigger signal resets flip-flop 27 and thus the signal on line 43a, shown as waveform 43, goes back to a low logic level at that time. As can be seen from FIG. 2, the circuits are now back in the initial condition, ready for the next cycle. Eventually, after the trigger signal cause an injection, there will be another data acquisition phase, and the process will repeat itself.

Figure 3:
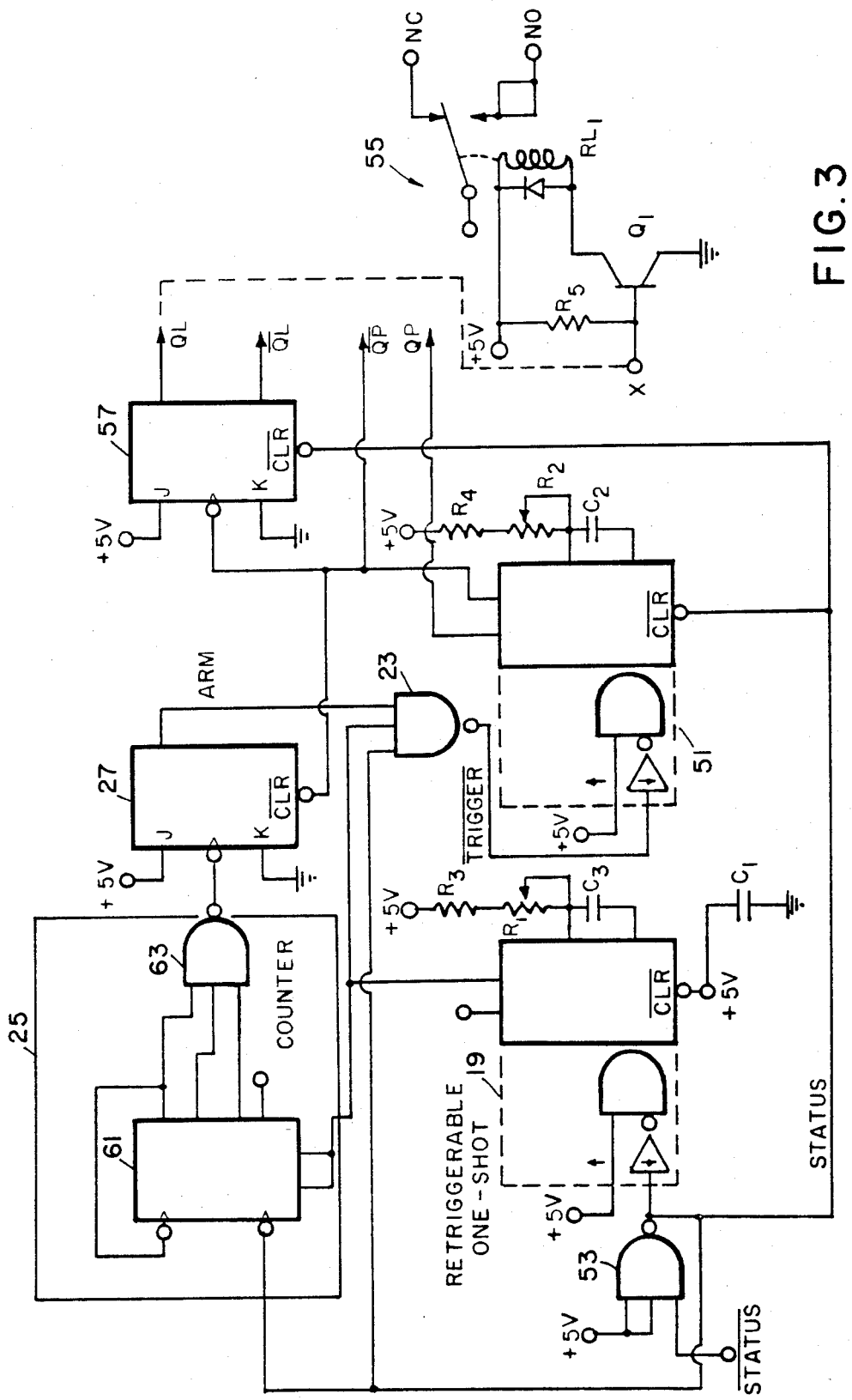
FIG. 3 is a logic diagram of a more detailed embodiment of the device of FIG. 1.

FIG. 3 is a logic diagram of a specific embodiment of the present invention. In this particular instance, the status signal indicating that the converter is ready to receive signals is an inverted signal, i.e., $\overline{STATUS}$. Thus, the signal is coupled through an inverter formed of a three-input NAND gate 53 with its two additional inputs tied to +5 volts. The $\overline{STATUS}$ signal provides the input to retriggerable, one-shot multivibrator 19, which is a conventional integrated circuit, having an external capacitor C3 and external resistor R3 which determine its time constant. In series with R3 is a trimmer potentiometer R1 for fine adjustment of the time period. This circuit, and the other circuits are provided with a +5 logic supply which is also coupled to the $\overline{CLR}$ input of the one-shot 19. A capacitor C1 to ground is provided in conventional fashion for filtering purposes. The $\overline{STATUS}$ signal is also provided to the $\overline{CLR}$ input of a second one-shot multivibrator 51 and to the $\overline{CLR}$ input of a flip-flop 57 for clearing these devices. It is also coupled to gate 23, in this case implemented as an NAND gate rather than an AND gate. It is also coupled to the count input of a divided-by-twelve counter 25 which is implemented utilizing a counter 61 and a NAND gate 63 for decoding the counter output. The output of NAND gate 63 provides the set input to flip-flop 27. The output of flip-flop 27, the $\overline{STATUS}$ signal and the output of one-shot 19 are the inputs to NAND gate 23. The output of one-shot 19 also provides the clear input to counter 61. The output of NAND gate 23 is an input to further one-shot multivibrator 51 which, similarly to multivibrator 19 has an external capacitor C2, resistor R4 and trimmer R2. The one-shot 51 provides a positive logic output and a negative logic output designated QP and $\overline{QP}$, respectively. The $\overline{QP}$ signal is a trigger input to flip-flop 57 which provides outputs QL and $\overline{QL}$.

Any of these outputs can be coupled into a relay circuit 55 utilized for isolation purposes, i.e., to separate the logic levels of the circuit of FIG. 3 from the auto-sampler 15 of FIG. 1. The relay circuit, as illustrated, includes a transistor Q1, having its base coupled to any one of the four outputs QL, $\overline{QL}$, $\overline{QP}$ and QP. The transistor has, in its emitter-collector path, a coil for a relay RL1. In conventional fashion, the base of transistor Q1 is biased through a biasing resistor R5 and a diode is coupled across the coil of the relay RL1 to provide protection. The relay contacts include a normally open contact, normally closed contact and center contact, thereby permitting any desired combination of signals in conjunction with the outputs QL, $\overline{QL}$, $\overline{QP}$ and QP.

In operation the negative logic $\overline{STATUS}$ signal is inverted in inverter 53. Thus, when the converter goes from a condition where it is capable of receiving data to a pulsing condition indicating that it is receiving data, a positive going edge will occur. This is inverted through inverter 53 and provided as an input to the retriggerable, one-shot 19 which responds to the negative going pulse to provide its output in the manner explained above. The negative logic output of one-shot 19 is coupled to the counter clear input and to the NAND gate 23. The counter 61 counts pulses and, when the desired count is reached and decoded by gate 63, an output is provided setting flip-flop 27. Thus, that input to NAND gate 23 will then be a high logic level. The signal $\overline{STATUS}$, which is now low, when inverted through inverter 53, will also be high, resulting in two high level signals. The third signal from the negative logic output of one-shot 19 will also go high once it times out. With three positive or high signals, the output of NAND gate 23 will go from a high level to a low level causing one-shot 51 to be triggered. On its output designated $\overline{QP}$ there will be a negative going pulse and on its output QP a positive going pulse. The output $\overline{QP}$ is utilized to set flip-flop 57 and to reset flip-flop 27. Thus, fixed logic levels QL and $\overline{QL}$ will be provided out of the flip-flop 57. Either the pulsed logic levels $\overline{QP}$ and QP or the fixed logic levels QL and $\overline{QL}$ can be utilized directly or through the relay circuit 55 for driving the auto-sampler or other devices requiring timing signals of this nature.

What is claimed is:

1. An automatic device for use in an instrument which includes a means responsive to a trigger signal to initiate an event; and a data acquisition means adapted to receive and convert data resulting from that event, said data acquisition means having a status output which is in one state when it is available to receive data and in another state when it is not available to receive data and which is pulsed during a conversion cycle; said automatic timing device synchronizing operation of the means responsive to trigger the data acquisition means comprising:

(a) means to count the pulses occurring during a conversion cycle and provide a first output signal when a predetermined count is reached;
(b) means for providing a second output signal a predetermined time after a last pulse is received; and
(c) means for ANDING said status signal in said one state, said first output signal, and said second output signal to provide a trigger output when all three of said signals are present, whereby said trigger signal will be provided only when said data acquisition means are available to receive an input and data acquisition is not in progress.

2. The device according to claim 1, wherein said means for providing said first signal comprise a divide-by-n counter and a flip-flop having an input coupled to the output of said counter whereby said flip-flop will be set after n counts and provide at its output said first signal.

3. The device according to claim 2, wherein said means for providing said second output signal comprises a first retriggerable, one-shot multivibrator having a time period greater than the time between said pulses from said data acquisition means whereby after being triggered by a first pulse, said one-shot multivibrator will maintain its state until a predetermined time period after the last pulse of a sequence.

4. The device according to claim 3, wherein said ANDING means comprise a NAND gate.

5. The device according to claim 4, wherein the output of said first one-shot is coupled as a clear input to said counter.

6. The device according to claim 5, wherein the output of said adding means is coupled as a clear input to said flip-flop.

7. The device according to claim 6, and further including a second one-shot multivibrator having its input coupled to the output of said adding means, an output of said second one-shot multivibrator being coupled as a clear input as the clear input to said flip-flop.

8. The device according to claim 7, and further including a further flip-flop having its input coupled to the output of said second multivibrator whereby said flip-flop will be set by the output of said second multivibrator to provide a fixed logic level signal, said multivibrator providing a pulsed signal.

9. The device according to claim 8, wherein each of said second multivibrator and further flip-flop provide both negative and positive logic outputs.

10. The device according to claim 9, wherein said status signal is coupled to reset said second multivibrator and further flip-flop whereby, upon the transition occurring when pulsing begins, said second multivibrator and further flip-flop will be cleared.

11. The device according to claim 10, and further including output isolation means adapted to couple any of said fixed and pulse logic levels to a device being controlled.

12. The device according to claim 11, wherein said isolation means comprise a relay and a driving means for said relay.

13. The device according to claim 12, wherein said driving means comprise a transistor.

14. The device according to claim 1, wherein said instrument comprises a chromatograph.

15. The device according to claim 14, wherein said instrument comprises a gas chromatograph and said trigger output is coupled to operate an auto-sampler.

16. The device according to claim 1, wherein said data acquisition means comprises a digital-to-analog converter.

17. A method generating triggering signals to initiate an event during which event data acquisition takes place such that the triggering and data acquisition are synchronized, the data acquisition being accomplished by means which provide an output at one level when data acquisition is possible, at another level when data acquisition is not possible and pulses when data acquisition is taking place comprising:
(a) counting the pulses when they occur until a predetermined number of counts is reached and then providing a first output;
(b) providing a second output a predetermined amount of time after a pulse occurs, said predetermined amount of time being greater than the time between pulses; and
(c) providing a triggering signal if said output of said data acquisition means is at said first level and said first and second signals are both present.

* * * * *